United States Patent [19]

Chu et al.

[11] Patent Number: 4,888,366

[45] Date of Patent: Dec. 19, 1989

[54] INDUCTIVE COLLAGEN-BASED BONE REPAIR PREPARATIONS

[75] Inventors: George Chu, Sunnyvale; Ranga Nathan, Newark; Saeid Seyedin, Mountain View, all of Calif.

[73] Assignee: Collagen Corporation, Palo Alto, Calif.

[21] Appl. No.: 100,990

[22] Filed: Sep. 25, 1987

Related U.S. Application Data

[63] Continuation-in-part of Ser. No. 816,268, Jan. 6, 1986, which is a continuation-in-part of Ser. No. 664,158, Oct. 24, 1984, Pat. No. 4,563,350.

[51] Int. Cl.$^4$ ............................ A61F 2/02; A61F 5/04
[52] U.S. Cl. ..................................... 523/115; 424/423; 424/95; 623/16; 606/76
[58] Field of Search ................. 530/350, 840; 424/95, 424/423; 106/122, 35; 128/92 YQ; 623/16; 523/115

[56] References Cited

U.S. PATENT DOCUMENTS

| | | | |
|---|---|---|---|
| 4,294,753 | 10/1981 | Urist | 530/840 |
| 4,394,370 | 7/1983 | Jefferies | 424/95 |
| 4,434,094 | 2/1984 | Seyedin et al. | 530/840 |
| 4,440,750 | 4/1984 | Glowacki et al. | 424/95 |
| 4,596,574 | 6/1986 | Urist | 424/14 |

OTHER PUBLICATIONS

Urist et al, "Purification of Bovine Bone Morphogenetic Protein by Hydroxy-Apatite Chromatography", *Proc. Natl. Acad. Sci. USA,* Jan. 1984, vol. 81, pp. 371–375.

Termine et al, "Mineral and Collagen-Binding Proteins of Fetal Calf Bone", *J. Biol. Chem.,* vol. 256, No. 20, Oct. 25, 1981, pp. 10403–10408.

*Primary Examiner*—John Kight
*Assistant Examiner*—Nathan M. Nutter
*Attorney, Agent, or Firm*—Irell & Manella

[57] ABSTRACT

An improved process for the preparation of mineral/-collagen/OF (osteogenic factor) inductive implants for bone repair utilizes drying, under ambient pressure conditions, a suspension of 75–95% mineral particles, 5–25% collagen, and an effective amount of OF, such as 0.5–4% partially purified OFE or its equivalent wherein the concentration of collagen in the suspension subjected to drying is 30–100 mg/ml. The resulting implants are improved. They are homogeneous in composition and have a high compressive modulus as well as containing OF in a biologically active and available form.

20 Claims, 6 Drawing Sheets

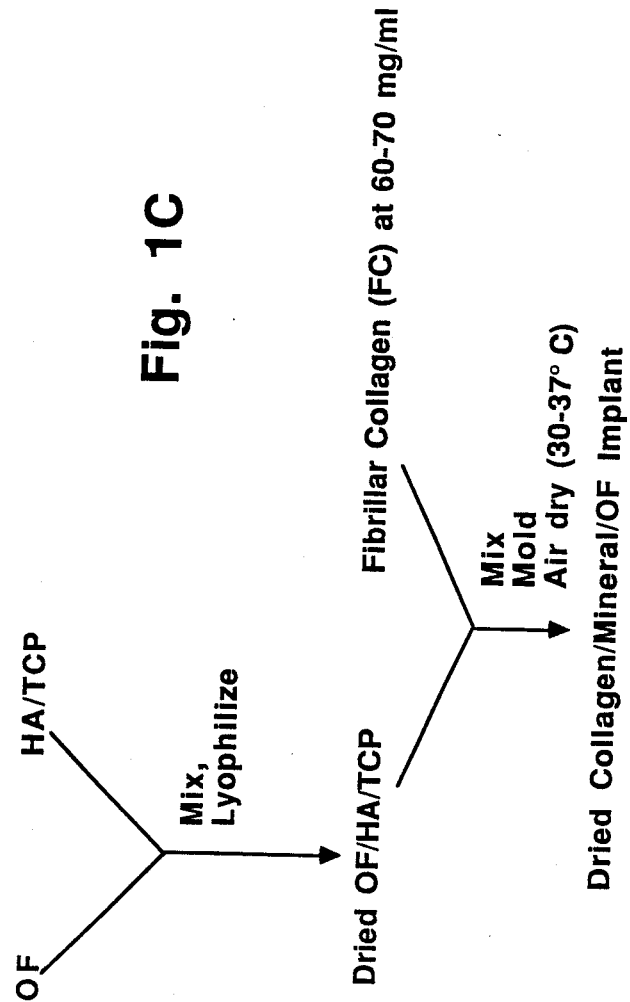

Example 2: LYO. OFE/NFE/CERAMIC

Example 3: DRIED OFE/FC/CERAMIC

Example 2: LYO./OFE/NFE/CERAMIC

Example 3: DRIED/OFE/FC/CERAMIC

Example 2: LYO./OFE/NFE/CERAMIC

Example 3: DRIED/OFE/FC/CERAMIC

INDUCTIVE COLLAGEN-BASED BONE REPAIR PREPARATIONS

This is a continuation-in-part of U.S. Ser. No. 816,268 filed 6 Jan. 1986 which is a continuation-in-part of U.S. Ser. No. 664,158, filed 10/24/84, now U.S. Pat. No. 4,563,350, issued 7 Jan. 1986.

TECHNICAL FIELD

The invention relates to a process to prepare bone repair materials and to the materials so prepared. More specifically, it relates to the preparation of collagen/mineral supports containing chondrogenic/osteogenic proteins.

BACKGROUND ART

It is well recognized that the physiological repair of bone defects and fractures is mediated by factors which encourage the differentiation of cells and the formation of the mineral components of bone. Recently, attempts have been made to identify the factor or factors which are significant in these activities. U.S. Pat. Nos. 4,440,750 and 4,430,760 disclose the use of demineralized bone powder (DMB) to substitute for whatever naturally occurring factors are required in implants or by injection. U.S. Pat. Nos. 4,294,753 and 4,455,256 to Urist disclose a bone morphogenic protein (BMP) which is extracted from demineralized bone using urea or guanidine chloride, and then reprecipitated. Further purifications of this factor have been reported by Urist in *Clin Orthop Rel Res* (1982) 162: 219; *Science* (1983) 220: 680; and *Proc Natl Acad Sci* (USA) 81: 371. Osteogenic factor proteins which have characteristics different from those described by Urist for BMP were isolated from DMB and purified by Seyedin and Thomas (U.S. Pat. No. 4,434,094; U.S. Pat. No. 4,627,982).

Since the foregoing factors aid in the reformation of bone, it has been desirable to include them in compositions administered for bone repair. In U.S. Pat. No. 4,440,750 (supra) a reconstituted atelopepetide collagen preparation was used as a carrier for either DMB or a DMB extract. U.S. No. 4,394,370 to Jefferies discloses a nonatelopeptide collagen composition as a carrier for crude extract of DMB, which is referenced to the Urist publications.

Additional work has been done by Reddi, et al, *Proc Natl Acad Sci* (1983) 69: 1601 which describes the use of allogenic demineralized bone powder in rat-host animals; Sampath, T. K. et al (*Proc Natl Acad Sci* (USA)) (1983) 80: 6591 reported further purification of the osteogenic factors from a number of species.

U.S. Pat. No. 4,563,350 (of which this is a continuation-in-part) describes the use of a collagen bone repair composition which, however, requires the presence of nonfibrillar collagen to deliver the inductive activity effectively. The parent application to the herein specification, U.S. Ser. No. 816,268, filed 6 Jan. 1986, assigned to the same assignee and incorporated herein by reference, describes compositions containing, in addition to hypoimmunogenic nonfibrillar or fibrillar collagen, at least 75% wt/wt of mineral for hard tissue implants. The preparations described in that application are prepared by processes which do not require, and do not recognize the desirability of, adequate intimate mixing under conditions which prevent separation of the collagen and mineral components of the carrier. In suggested preparations described in that application, collagen in solution at approximately 3 mg/ml, which also contains the osteogenic factor is mixed with solid mineral powder and the resulting material is lyophilized. In the alternative, a paste is prepared using a lyophilized mixture of mineral with the osteogenic factor and this is added to a 65 mg/ml Zyderm ® collagen implant fibrillar collagen suspension.

Collagen/mineral preparations for conductive repair of bone—i.e., matrices which permit the ingrowth of new cartilage and bone cells, but without the introduction of exogenous osteoinductive factors have also been described. U.S. Ser. No. 848,443, filed 4 Apr. 1986, which is a continuation-in-part of U.S. Ser. No. 717,072, now abandoned, assigned to the same assignee and incorporated herein by reference, describes the preparation of wet and dry mixtures of mineral and atelopeptide collagen which contain 60-98% by weight of mineral and 2-40% of collagen. The compositions are prepared by a mixing the collagen suspension at 65 mg/ml with the solid powdered mineral. The resulting mixtures are either used as a paste, or are allowed to dry at ambient temperature and pressure.

U.S. No. 4,485,097 to Bell describes a collagen lattice containing fibroblast cells and demineralized bone powder. However, this has no mineral content.

U.S. Pat. No. 4,097,935 describes a hydroxyapatite ceramic material which can be mixed with collagen to obtain a bone replacement mixture.

None of the foregoing compositions result in a homogeneous, rigid preparation which can be used directly for implantation in bone, and which is effective in the mediation of bone repair by effective delivery of the included osteogenic factors.

DISCLOSURE OF THE INVENTION

It has now been found that dry prostheses which are effective carriers for osteogenic factors can be obtained which are homogeneous, strong, and capable of inducing the ingrowth of bone by virtue of the osteogenic factors contained therein. This result is achieved by first mixing a solution of the osteogenic factor preparation with either the collagen or mineral component, and then combining the remaining component with the mixture in a preparation wherein the collagen concentration in the total suspension is of the order of 30-100 mg/ml. This mixture is then dried at ambient pressure, and at slightly elevated temperatures. When the preparation process is conducted in this way, the resulting compositions are characterized as being rigid with a compressive strength of at least 20 Newtons per square centimeter ($N/cm^2$) and containing a uniformly distributed and biologically active and available inclusion of osteogenic factor. They are also hypoimmunogenic.

Thus, in one aspect, the invention is directed to solid bone repair compositions which consist essentially of a mixture of 60-98%, preferably 75-95%, by weight of a calcium phosphate particulate mineral component, 2-40%, preferably 5-25%, of an atelopeptide purified collagen preparation and an effective amount of osteogenic factor (OF). One measure of an effective amount corresponds to the activity obtained by including about 0.5-4% of a "partially purified" osteogenic factor extract (OFE). Both the factor and the carrier are sufficiently pure to be hypoimmunogenic. The OFE is sufficiently concentrated in activity that only the cited maximum of 4% wt/wt of OFE in the preparation is required. The compositions have the characteristics of homogeneity with regard to the distribution of all three components, biological activity and availability of the contained OF, and a compression modulus of at least 20 N/cm².

In other aspects, the invention relates to processes to prepare these compositions. In general, these processes are characterized by the admixture of the components of the mixture in a suspension wherein the concentration of collagen is 30-100 mg/ml before controlled drying, and subjecting this suspension to drying under ambient pressure until the water content is sufficiently reduced that a solid material is obtained.

BRIEF DESCRIPTION OF THE DRAWINGS

FIG. 1C is a diagrammatic representation of an embodiment of the process of the invention wherein OF and mineral are premixed, lyophilized and then supplemented with fibrillar collagen.

MODES OF CARRYING OUT THE INVENTION

A. Definitions

Figure 1A:
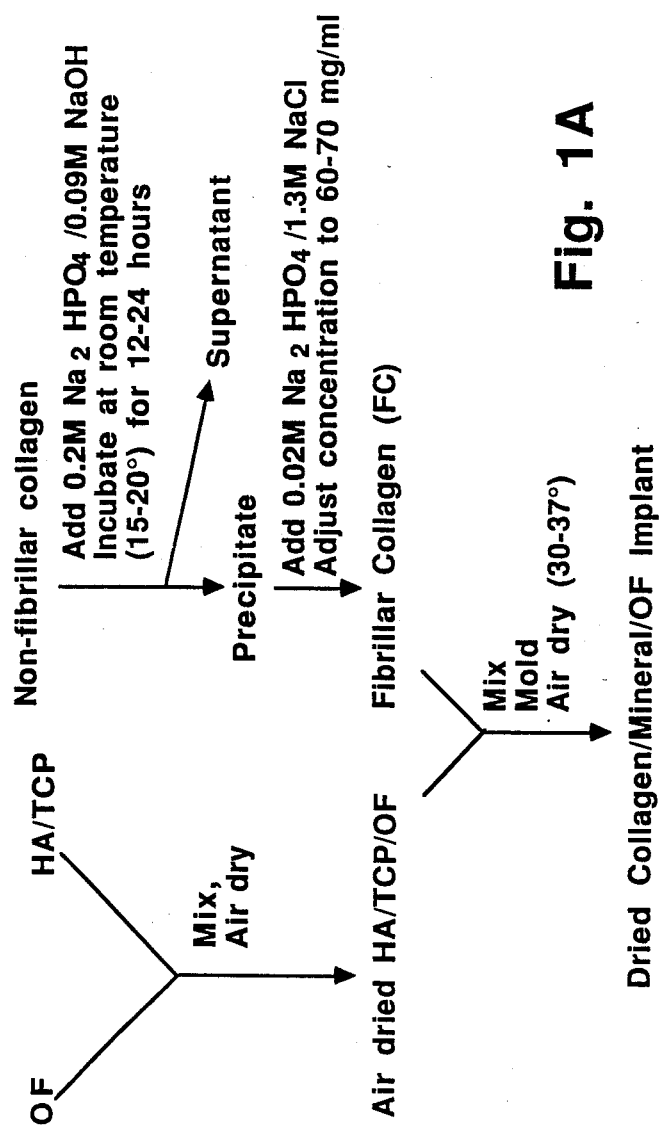
FIG. 1A is a diagrammatic representation of an embodiment of the process of the invention, wherein OF and mineral are premixed, air dried, and then supplemented with fibrillar collagen.

As used herein, "osteoinductive" and "osteogenic" are used interchangeably and refer to conversion of bone progenitor cells into living osseous tissue. The induction may result in osteogenesis—i.e., direct formation of mineralized bone through secretion of the organic and inorganic components of bone, or the osteoinduction may also involve intermediate formation of cartilage—i.e., the osteoinductive factor may also be chondrogenic. Indeed, proteoglycan which is diagnostic for cartilage formation, is used as an index of osteoinductive activity of the compositions of the invention.

"Derived from" when referred to the osteogenic factors herein refers to a structural relationship or homology. It is not limited to physical derivation. Thus osteogenic factor "derived from" bone indicates that the factor or factors has an amino acid sequence homologous and similarly functional to those of factors natively produced in bone tissue; it does not necessarily mean that the material used is directly isolated from bone per se. It might, for example, be made synthetically, or by using recombinant DNA techniques.

"Hypoimmunogenic" refers to an acceptable biocompatibility. It is understood that many substances may be immunogenic in some animals and applications but are not able to raise detectable levels of specific immunoglobulins in others. It is also understood that complete absence of specific immunoglobulins and of inflammation may not be required. Thus, when used to describe the composition components or the compositions of the invention, "hypoimmunogenic" is functionally defined to mean that any immune responses are within acceptable levels.

"Atelopeptide collagen" refers to collagen which has been suitably treated so as to remove or partially remove the telopeptide, or immunogenic portions.

Briefly, and in explanation, collagen comprises a fibrillar structure composed of bundles of triple helical configurations of repeating amino acid sequences. These triple helical sequences are terminated by non-helical structures, "telopeptides" which are responsible both for the cross-linking between various collagen chains, and, in part, for the immunogenicity of collagen preparations. Removal of these structures can be accomplished by treating with suitable proteolytic enzymes such as trypsin. The resulting atelopeptide collagen is more suitable for xenogeneic use, as the major species-specific immunogens have thus been removed.

"Non-fibrillar collagen" has been treated so as not to maintain its native fibrillar structure. This term thus refers to collagen which has been solubilized and has not been reconstituted into its native fibrillar form. The fibrillar construction can be disrupted by dissolution; it can be returned to solid form either by reconstituting the fibers (fibrillar) or by non-specific aggregation (non-fibrillar).

"OFE" or osteogenic factor extract designated as "partially purified OFE" is defined as the partially purified extracts from bone described hereinbelow, which is the <30,000 low MW fraction, bound to and removed from a cation exchange resin, as described in U.S. Pat. No. 4,627,982, incorporated herein by reference. Percentages of OFE in the compositions of the invention are given in terms of the "partially purified" preparations described. However, it is understood that other methods of preparation which yield comparable amounts of osteogenic activity may also be used, if sufficiently pure to be hypoimmunogenic. The osteogenic activity of these extracts is due to the presence of one or more osteogenic factors (OF) contained therein. The provision of this factor or factors (OF) to the compositions can be made in the form of the extract (OFE), or synthetic forms of the factor or factors may be used, or a combination thereof. Of course, OFE or OF preparations of greater purity than that referenced as "partially purified" can be used in an amount corresponding at a similar activity level to that specified herein.

"OF" is defined as the factor(s) per se responsible for the osteogenic activity of the extract, whether obtained from the extract or synthesized chemically. OF also includes variants of the naturally occurring materials which retain the osteogenic activity and pharmacological behavior of the native material, i.e. remain bioavailable in the compositions of the invention.

Thus, "a percentage of OF equivalent to partially purified OFE" refers to an amount of an OF preparation which provides the activity obtained by the use of the "partially purified OFE" as defined above at percentages of 0.5-4%. In general, the equivalent amount will be in the range stated or less, as similarly purified or more highly purified preparations would be required in order to achieve the level of hypoimmunogenecity necessary for use in allogenic or xenogenic recipients. If highly purified extract or synthetic material is used, a smaller percentage will be effective.

"Agitation" of mixtures according to the process of the invention refers to mechanically effecting motion of the particles of the mixture by, for example, conventional means such as stirring, shaking, vortexing and the like.

"Incubating" means holding a subject material or mixture for a given time period under controlled or specified conditions, wherein the moisture content remains the same during this time period.

The percentages set forth herein for the invention compositions are weight/weight percentages of the dry, specified components. Although water is often (though not always) an important part of these compositions, its percentage is variable depending on the physical properties desired in the composition. The compositions are, for example, often stored dry and then implanted dry or rehydrated for implantation.

"Controlled drying" refers to a procedure for removing moisture which is conducted at approximately ambient conditions of pressure and temperature. Of course, it is not necessary to use air to maintain approximately atmospheric pressure; nitrogen, for example, could also be used. However, since there are no major stability problems with the compositions herein, air is the most convenient choice. The temperature may be slightly elevated over ambient conditions to hasten the drying process.

B. General Description

The compositions of the invention are mixtures of effective amounts of an osteoinductive factor (OF) preparation which is sufficiently purified to be hypoimmunogenic when used xenogeneically, with a hypoimmunogenic carrier such as the mineral/collagen carrier of the invention compositions. The percentage of a particular OF preparation needed in the composition will, of course, depend on the purity of the preparation, but for the "partially purified OFE" preparations as defined, a range of 0.5–4% is suitable. More highly purified OF could be used in correspondingly lesser amounts.

The OF Preparation

OF preparations which meet the criterion of sufficient purity to be hypoimmunogenic in xenogeneic hosts may be prepared in several ways. As sources for the factor, bone, dentin, osteosarcomas, or chondrosarcomas and other tissues of vertebrate origin containing OF can be used. It has been shown that preparations containing OF from human, monkey, bovine and rat are non-species specific in their ability to produce endochondral bone in xenogeneic implants by Sampath, T. K., et al, *Proc Natl Acad Sci* (USA) (1983) 80: 6591. Thus the OF which is usable in the mixtures of the invention may be derived from any of these sources, and, indeed, may be any protein having osteoinductive activity which is substantially similar to those proteins derived from vertebrate sources, whether thus prepared, modified by inadvertent or intentional means, prepared by chemical synthesis, recombinant DNA techniques, or other such procedures. For example, in addition, the bone morphogenic protein of Urist, if purified sufficiently, may perhaps also be used. The OF must meet the requirements only of substantial similarity to a protein derivable from a vertebrate source, osteoinductive functionality, and acceptably low immunogenicity.

One useful process for preparing the "partially purified OFE" useful in the compositions of the invention is described in U.S. No. 4,627,982 (supra). Briefly, it begins by treating porcine or bovine long bone materials (because of ready availability) with mechanical and abrasive techniques to clean and fragment them, and defatting by extraction with organic solvents such as ether or ethyl acetate, and then demineralizing usually by extraction with strong acid using standard techniques, and then using the resulting demineralized bone (DMB) as a starting material.

To obtain the solubilized OFE, the DMB is then extracted with a chaotropic agent. The extraction is preferably carried out at reduced temperatures in the presence of protease inhibitors to reduce the likelihood of digestion or denaturation of the extracted protein, for about 4 hr/1 day. After extraction, the extractant may be removed by suitable means such as dialysis against water, controlled electrophoresis, or gel filtration or any other suitable means. The extract, with or without the extractant removed, is then subjected to gel filtration or other sizing procedure to obtain fractions of molecular weight below about 30,000 daltons using standard techniques.

The low molecular weight fraction is freed from competing ions and is then subjected to ion exchange chromatography using either cation exchange, for example with CMC at approximately pH 4.5–5.2 in the presence of a non-ionic chaotropic agent such as urea, in order to obtain the "partially purified OFE", as above-defined, or using anion exchange, for example, with DEAE cellulose, in the presence of, for example, 6M urea and 20 mM sodium phosphate at approximately pH 7.2.

The OF is adsorbed to the cation exchange resin, and is eluted under suitable conditions; the active eluate fractions resulting from the cation exchange chromatography may be used directly as "partially purified OFE" in the compositions of the invention. The percentage range at 0.5–4% is based on a weight/weight percentage of the partially purified protein in the final composition.

The OF contained in the "partially purified OFE" can be further purified by precipitation in phosphate buffer at pH 6–8 by addition of 0.01–0.1M sodium phosphate. The precipitate is then redissolved in a nonionic chaotropic agent and chromatographed on a hydroxyapatite column by HPLC.

Alternatively, the non-adsorbed material resulting from subjecting the low MW fraction derived from DMB to treatment by anion exchange resin contains the OF activity, and this non-adsorbed protein, after dialysis to remove urea, may also be used at appropriate percentages as an equivalent of the "partially purified OFE". The protein in the anion exchange resin treated solution can be recovered by lyophilization, or stabilized by dialyzing against 0.01N HCl. (The "partially purified OFE" can also be subjected to treatment with the anion exchange resin as described above, using this as an additional, rather than an alternative step.)

Since the anion exchange treatment is not described in the issued '982 patent, details are set forth as follows:

The low MW from the gel, or the OF-containing fraction from cation exchange eluate, is dissolved in buffer containing 6M urea, 20 mM sodium phosphate, pH 7.2, 20 mM NaCl, and protease inhibitors. The solution is then run over a DEAE cellulose column equilibrated with the same buffer. The flow-through fraction, which contains the OF, is dialyzed against water to remove urea, and the OF recovered by lyophilization. Alternatively, the flow-through volume is dialyzed against 0.01N HCl, and stored in 0.01N HCl at a protein concentration of 1–10 mg/ml. These solutions are stable over several months and can be lyophilized.

It should be noted that partially purified OFE is described merely as a convenient source for OF—the factor(s) responsible for the osteogenic activity. The OF may also be obtained from other sources, such as, for example purified forms of the BMP of Urist, or synthetic materials. Synthetic materials may also include variants of the natural material which retain the bioactivity and bioavailability of the natural counterpart(s). The invention is directed to compositions effective in providing inductive bone growth, regardless of OF source.

The Carrier

The carrier portion of the preferred composition provides 60-90%, preferably 75%, and more preferably around 85-95%, of a mineral component to the composition and an additional component selected from fibrillar or non-fibrillar collagen or both.

The mineral component is generally selected from various forms of calcium phosphate, preferably hydroxyapatite (HA) and tricalcium phosphate (TCP) or most preferably, mixtures thereof. Both HA and TCP are commercially available, and selection can be made from a number of mesh sizes and porosities. These materials have been disclosed to be useful in the construction of hard tissue implants and are thus of suitable biocompatibility to comprise a portion of the composition of the invention. See, e.g. U.S. Pat. No. 4,314,380 which discloses HA preparations, and Hayashi, K. et al *Arch Orthop Traumat Surg* (1982) 99: 265 which discloses an alternate form of HA. For compositions which contain a mixture of HA and TCP, it is paticularly preferred that the mineral content be 95% or less, for HA alone, up to 98% can be used.

An attribute of the compositions of the invention is acceptably low immunogenicity. Accordingly it is preferable in general to use the atelopeptide forms of non-fibrillar or fibrillar collagen components. There may, however, be instances in which the presence of telopeptides, due to the configuration of the implanted composition, the susceptibility of the host, or some other reason, is not sufficiently detrimental to the hypoimmunogenicity to render the composition unacceptable. In other words, the use of atelopeptide collagens is preferred, but not necessarily required. Hypoimmunogenicity is especially important to permit use of xenogeneic sources of collagen. For example, by sufficiently diminishing immunogenicity, bovine or porcine collagen may be used in human subjects.

Non-fibrillar collagen can be supplied as a collagen-in-solution, or as a lyophilized form of collagen-in-solution which is non-specifically aggregated. A preferred source of the non-fibrillar collagen is collagen in solution (CIS) which is obtainable under the trademark Vitrogen® from Collagen Corporation, Palo Alto, Calif. However, any non-reconstituted collagen preparation may be used.

Fibrillar collagen can be derived from various sources, and a number of fibrillar collagen preparations are available in the art, wherein collagen derived from bone or skin of various mammals has been solubilized or dispersed in liquid medium and then recovered in fibrillar form. Preparations wherein the collagen is reconstituted into fibrils include, for example, Zyderm® collagen implant (ZCI), available from Collagen Corporation, Palo Alto, Calif. Other fibrillar preparations include Avitene®, which represents dispersed fibers that still have native fibrillar form; and Collagenfleece® which is a dispersed preparation subsequently freeze dried. (These latter preparations are not, therefore, "reconstituted".)

Characteristics of the Compositions

When prepared by the method described below, the compositions of the invention, which are 60-98%, preferably 75-95% particulate mineral, 2-40%, preferably 5%-25% collagen, and an effective amount of OF, such as that supplied by 0.5-4% partially purified OFE as defined above or its equivalent, will have certain desirable properties resulting from its mode of preparation. First, it should be noted that all of the components must be sufficiently pure or otherwise prepared so that the composition is hypoimmunogenic in the recipient. Second, the OF component must be uniformly distributed and biologically active and available. Finally, the mineral and collagen components must be homogeneously dispersed, the composition will be porous, and it will be hard rather than sponge-like; the compressive modulus is at least $20N/cm^2$.

Homogeneity as to the collagen/mineral components can effectively be assessed visually. Uniformity of the OF in the implant is assured by the preparation procedure; this can be verified by standard methods of analysis of portions of the sample. Bioavailability and activity of the OF is assessed by the ability of the implants to induce bone formation. A variety of methods are available for this assessment, most notably histological examination. In addition, the levels of alkaline phosphatase, as illustrated below, can be used to assess bone formation at a biochemical level. Other measures are also available, such as assessment of calcium levels and monitoring of cartilage formation by assay for proteoglycan. If desired, the hypoimmunogenicity of the implants can be ascertained by monitoring the serum levels of the recipient for antibodies reactive with the implanted materials or its components.

For assay of the compressive modulus, commercially available equipment, such as Instron ® universal testing model 4202 can be used, for example, according to the guidelines for measurement for compressive modulus as published by the American Society for Testing Materials.

To conduct this measurement, the compositions are first soaked for 5-24 hr in physiological saline. The soaking is done for a sufficient time to insure complete wetting; the composition is then placed in the test apparatus. If the material is resilient, it will compress easily until a point is reached wherein, in order further to compress the material, it is necessary to disrupt the inherent structure at the microscopic level. If the material is rigid, this point will be reached with less deformation than for resilient material. For collagen/mineral mixtures, the microscopic organization is maintained first by the triple helix per se, but also by interaction between the collagen triple helical portions of the individual components of the fibrils as well as binding of the fibrils to each other. Compression disrupting any of these levels of organization will be more difficult than general compression which decreases the volume of empty space. Of course, the more highly organized and cross-linked the collagen chains in the composition, the more difficult this microscopic compression is.

Thus, a high compressive modulus (measured in $N/cm^2$) indicates a high level of organization at the microscopic level, specifically, a high level of cross-linking between collagen molecules. A low compressive modulus indicates that cross-linking is low. For appropriate physical handling properties and for maintenance of integrity as an implant, it is important that the compressive modulus be reasonably high, at least about $20N/cm^2$ or more. The upper levels of compressive modulus are imposed by the nature of the materials, and it is believed that compositions of this type cannot, in fact, attain modulus values of much greater than 100N/cm$^2$ under any degree of cross-linking. In any event, it is significant in maintaining suitable physical properties for the compositions of the invention that the compressive modulus be above 20N/cm$^2$, and a preferred range is 20-30N/cm$^2$. (If a higher strength is desired, the composition can be heat cured, as described below, to obtain a compressive modulus of 50-60N/cm$^2$.) The resultant composition prepared according to the process of the present invention is assessed by this measure in order to verify that the required compressive resistance strength is attained.

Preparation of the Compositions

In the process of the invention, the composition is prepared in such a manner that a solid homogeneous preparation of high compressive modulus with bioavailable OF is obtained. In order to achieve this result, the final drying step for the composition must be conducted using a mixture which contains a suspension of collagen at a concentration of 30-100 mg/ml, the required amount of mineral, and the OF uniformly distributed in the suspension. This material must be dried at substantially ambient pressure, preferably at slightly elevated temperatures. Drying by lyophilization at the final step produces a spongy product nonconforming with regard to strength and homogeneity.

Accordingly, in the process required to achieve the compositions of the invention, a suspension containing 30-100 mg/ml of hypoimmunogenic, preferably atelopeptide, preferably reconstituted fibrillar collagen, sufficient to result in a final percentage of collagen of 2-40%, preferably 5-25%, in the composition, and sufficient particulate mineral to result in a final percentage of mineral of 60-98%, preferably 75-95%, along with sufficient OF to comprise the equivalent in activity of inclusion of 0.5-4% of the partially purified OFE preparation is agitated, molded into the desired shape, and dried under controlled conditions as described herein. Drying under controlled conditions continues until a moisture content is reached which results in a solid material having a compressive modulus of at least 20N/cm$^2$.

To prepare a composition with greater physical strength, e.g., with a compressive modulus of about 50-60N/cm$^2$, the above resultant is subjected to a heat curing process at 50°-120° C., preferably 75°-90° C. for 4-168 hours.

To begin the preparation, a diluted aqueous solution of OF, in some embodiments in mild acid, is mixed with all or a portion of the carrier. As the carrier consists essentially of a mineral and a collagen component, the OF may be mixed with either the collagen or mineral preparation in a preliminary step or the OF may be mixed into a suspension of carrier.

In general, the mineral is added as a particulate. The collagen is added initially as a suspension or gel (fibrillar collagen, FC) or solution (nonfibrillar collagen, NFC).

In one protocol, OF is mixed with the collagen in a preliminary step, and the mixture is incubated at room temperature for about 12-24 hours, harvested by centrifugation, and resuspended so that the collagen concentration is adjusted to the 30-100 mg/ml range with a buffer solution. The suspension is then mixed with the mineral component with agitation, molded into the desired shape and then subjected to controlled drying at low or ambient temperaturre. Alternatively, the mineral is added with agitation in a preliminary step and the mixture is subjected to controlled drying at low or ambient temperature. The collagen component is then added to form a cohesive mass having the prescribed concentration of collagen, molded into the desired shape, and then subjected to controlled drying.

In related protocols, a portion, for example, one-half or one-third or three-fourths of the total of either or both collagen and/or mineral components can be added in a preliminary step and the remainder afterwards. The portion of each component added need not be the same.

Controlled drying serves to integrate the OF into the carrier and to maintain homogeneity. The conditions of controlled drying as they relate to time and temperature are, of course, interdependent; however, in general, ambient temperatures are preferred. Suitable temperatures are in the range of 1°-40° C., preferably about 15°-37° C. Under these conditions, effective times range from 10-20 hours, or overnight for convenience.

In the controlled drying process, the suspension is subjected to an active or passive stream of gas, preferably air, but also, for example, an inert gas such as nitrogen, until perceptible moisture is lost. The dried product can then be stored, can be rehydrated for use if reshaping is needed, or can be used directly.

The following represent typical exemplary protocols; FIG. 1 shows a schematic for three particularly preferred processes of the invention.

In FIG. 1a, an OF preparation in dilute solution is mixed with the appropriate amount of mineral, preferably a porous HA/TCP mixture and thoroughly mixed. The material is then air dried to obtain a thoroughly integrated mixture of mineral and OF. The relative amounts are chosen to obtain the required activity of OF in the finished composition according to the level of purification of the OF extract.

The collagen component is then supplied as a collagen suspension at 60-70 mg/ml of reconstituted fibrillar atelopeptide collagen. The collagen at this concentration can be supplied as commercially available Zyderm ® Collagen Implant or as shown in FIG. 1a, can be prepared using standard procedures from collagen-in-solution by incubation with an appropriate concentration of basic phosphate buffer and recovery of the precipitate with appropriate dilution at neutral pH to achieve the desired concentration. The collagen component and the mineral/OF mixture are then combined so that the percentage of mineral in the total mixture is 60-98%, preferably 75-95%, and of collagen 5-25%, along with sufficient OF to obtain the activity of 0.5-4% of the partially purified OFE preparation. These materials are thoroughly mixed with agitation and molded to the desired shape before air drying at a suitable temperature.

Figure 1B:
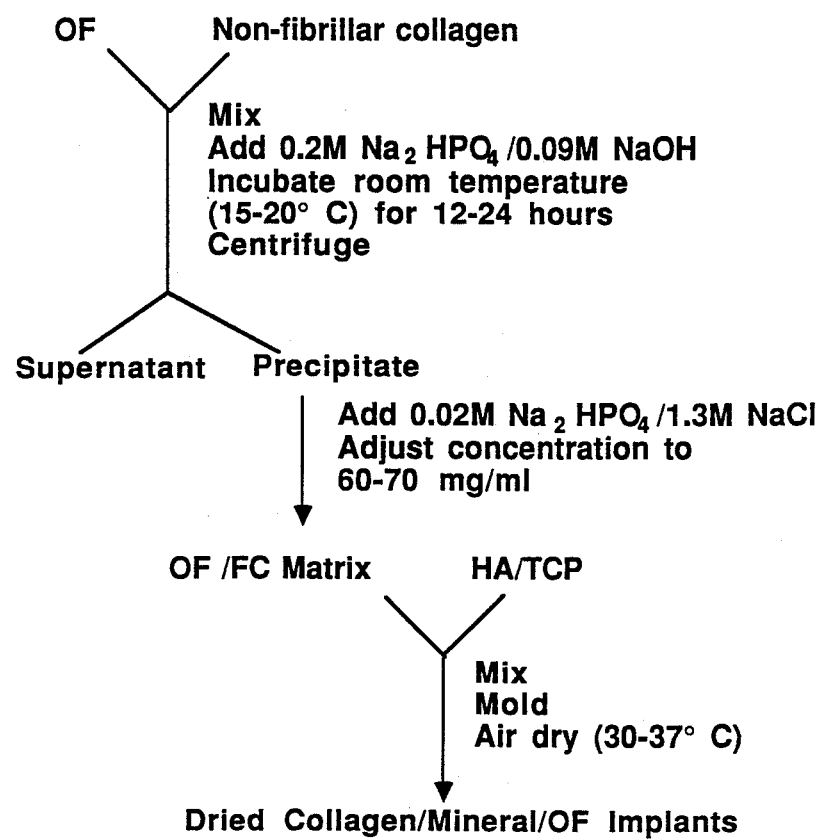
FIG. 1B is a diagrammatic representation of an embodiment of the process of the invention wherein fibrillar collagen and OF are premixed and mineral is added.

In an alternative procedure, shown in FIG. 1b, the OF preparation is combined with collagen in solution (nonfibrillar). The diluted collagen is then reconstituted by treating with 1/10 volume of 0.2M phosphate buffer to form a precipitate which includes the OF. The pH of the phosphate buffer is chosen to give a final pH of 7.0-7.5. After a suitable incubation period at ambient temperature, i.e., around 12-24 hr, the precipitate is centrifuged and recovered. After adjusting the concentration to a suitable level—i.e., between 30-100 mg/ml the collagen matrix containing OF is mixed with the particulate mineral, molded, and air dried at a suitable temperature to obtain the desired solid implant.

As shown in FIG. 1c, a thorough mixture of mineral and OF preparation can be dried by lyophilization to obtain solid mineral/OF which is then mixed with fibrillar collagen at suitable concentration for molding and air drying.

Other protocols can, of course, be used so long as the final mixture which, subjected to the process of controlled drying, contains a uniform homogeneous mixture of the composition of the required proportions with sufficient water in the suspension that the collagen is contained at a level of 30–100 mg/ml.

The compositions of the invention are molded into the proper shapes to be used as onlay grafts, in bone reconstruction, in the treatment of fractures and in other orthopedic indications such as spinal fusions. The methods for utilizing solid compositions to form such implants, and surgical methods for implanting them, are well understood in the art, and the compositions of the invention are useful in employing these standard means.

When placed in the desired location, the implant composition provides a matrix for the ingrowth of new cartilage and bone, as well as stimulating the production of these materials by virtue of the presence of osteoinductive factor.

Use of the Compositions

The compositions of the invention are used in a manner generally known in the art to repair major or minor defects in bone caused by trauma, disease, or congenital defects.

As described in the specific examples below, these compositions when implanted subcutaneously in xenogeneic hosts, are capable of stimulating bone tissue formation. Their capacity to do so can be verified by explanting the composition, and assessing the explant histologically, for cartilage proteoglycan formation, for the presence of calcium and for the presence of alkaline phosphatase. (Cartilage proteoglycan is a measure of cartilage formation; alkaline phosphatase is a marker of calcifying hypertrophic cartilage.) In addition, the host organism is shown to be free from antibodies reactive against the implanted material.

C. Examples

The following examples are intended to illustrate the invention. Alternative methods for preparing the components of the composition and for preparing the composition itself are within the scope of the invention, provided the resulting composition falls within the scope of the appended claims.

EXAMPLE 1

Assay of Inductive Implants
Implantation

Samples were implanted subcutaneously in the ventral thoracic region of 30–34 day old male Sprague-Dawley rats. Each rat received two implants of the same material on lateral sides, and explants for testing were removed at 14 and 28 days. The explants were assayed by histology and by assay for alkaline phosphatase activity.

Characterization of Explants-Histology

Explants which had been removed after 14 and 28 days were subjected to histological assessment by fixing in 10% neutral formalin for 26 hr, and then processing for paraffin embedding. 4–6 micron sections were taken from the imbedded tissues and were subsequently stained with either hematoxylin-eosin or with Saphranin-O ®. Saphranin-O ® is selective for cartilage proteoglycan.

Analysis for Alkaline Phosphatase

Alkaline phosphatase levels can be used as an indicator of bone formation. To determine alkaline phosphatase (AP), the explants were cut in small pieces and homogenized in 3 ml ice cold 1.5M NaCl, 3 mM NaHCO$_3$, pH 7.5. The homogenized samples were then centrifuged at 12,000 rpm for 50 min at 4° C., and an aliquot of the supernatant diluted 1:10 in cold distilled water. The method of Huggins, et al, *J Exp Med* (1961) 114: 761 was used to assess alkaline phosphatase using polystyrene plates.

Non-Immunogenicity of the Implants

Sera are removed from the implanted animals after 28 days, and assayed for the presence of antibodies against the implanted material using an enzyme linked immunosorbent assay (ELISA) technique; Microtiter wells are coated with 2–5 g of each of the components of the composition in 20 mM carbonate buffer (100:1) pH 9.6 at 4° C. overnight. The wells are washed 3 times with PBS containing 0.05% Tween 20 surfactant so as to remove unbound antigen.

Sera are then added for 2 hr at room temperature, and the wells washed 3 times with PBS-Tween 20 surfactant. Goat anti-rat IgG conjugated with horseradish peroxidase (1:2000 dilution) is added, and the wells incubated for 1.5–2 hr at room temperature. Unbound labeled antibody is then removed with PBS-Tween 20 with surfactant, and peroxidase substrate is added. The plates are incubated at room temperature for 30 min and the plates then scanned for optical density.

Extractable Calcium Determination

The formation of bone can also be assessed by determination of calcium. Explants are cut in small pieces and suspended in 1:10 (m/v) and 1:20 (m/v) of 0.5N HCl to dissolve the bone. The samples are incubated for another 5 days at room temperature and centrifuged at 12,000 rpm for 40 min, and the calcium concentration of the supernatant determined by atomic adsorption (Trace Analysis Laboratory, Hayward, Calif.).

EXAMPLE 2

Preparation of Lyophilized Inductive Compositions

Partially purified OFE was used as a 3 mg/ml solution in 0.01N HCl.

A 5.4 ml sample of the OFE solution was stirred with 22 ml Vitrogen ® CIS at 4° C. for 5 min; 569 mg of porous HA/TCP ceramic in particulate form, obtained from Zimmer Corp, Warsaw, IN, was added and the mixture incubated at 4° C. for 5 min, and then lyophilized. The resulting solid was 87.5% ceramic, 10% nonfibrillar collagen (NFC), 2.5% OFE; all percentages representing solids by weight. The composition prepared by this method is designated in FIGS. 2 and 3 as "Example 2" (see Example 5). A control preparation was made identically, but using 0.01N HCl instead of OFE solution.

EXAMPLE 3

Preparation of Control-Dried Inductive Compositions

Partially purified OFE was used as a 3 mg/ml solution in 0.01N HCl. A 5.4 ml sample of the OFE solution was stirred with 569 mg of HA/TCP, obtained from Zimmer, Corp., Warsaw, IN at 20° C. for 5 min and then air dried at 37° C. The resulting solid was thoroughly mixed with 1.0 ml of 65 mg/ml Zyderm ® Collagen Implant (fibrillar collagen) and air dried again at 37° C. to dryness. The resulting solid was 87.5% ceramic, 10% fibrillar collagen, and 2.5% OFE; all percentages representing solids by weight. The composition is designated as "Example 3" in FIGS. 2 and 3. A control preparation was made identically, but using 0.01N HCl instead of OFE solution.

EXAMPLE 4

Alternative Method for Preparation of Control-Dried Inductive Compositions

Partially purified OFE was used as a 3 mg/ml solution on 0.01N HCl. A 6.5 ml sample of the OFE solution was stirred with 25 ml of 3 mg/ml Vitrogen ® collagen-in-solution and 3.5 ml 0.2M $Na_2HPO_4$/0.09M NaOH pH 11.2. The mixture was incubated at ambient temperature for 16-20 hr, i.e., overnight for convenience. The resulting coprecipitate of OFE and fibrillar collagen (FC) was harvested by centrifugation at 13,000×g for 30 min. The protein concentration of the co-precipitate was adjusted to 65 mg/ml with PBS.

The OFE and FC co-precipitate at 65 mg/ml was mixed with 569 mg of HA/TCP, obtained from Zimmer, Corp., Warsaw, IN, and air dried at 37° C. to dryness. The resulting solid was 87.5% ceramic, 10% fibrillar collagen, and 2.5% OFE; all percentages representing solids by weight. A control preparation was made identically but using 0.01N HCl instead of OFE solution.

EXAMPLE 5

Comparison of Various Inductive Compositions
Implantation

The material prepared according to Example 2 (lyophilized OFE/NFC/ceramic) was hydrated with approximately half volume of water, allowed to soak for 5 min, and molded into desirable dimensions prior to implantation.

The material prepared according to Example 3 (air dried OFE/FC/ceramic) was implanted in the dry form.

Bone Formation

Figure 2:
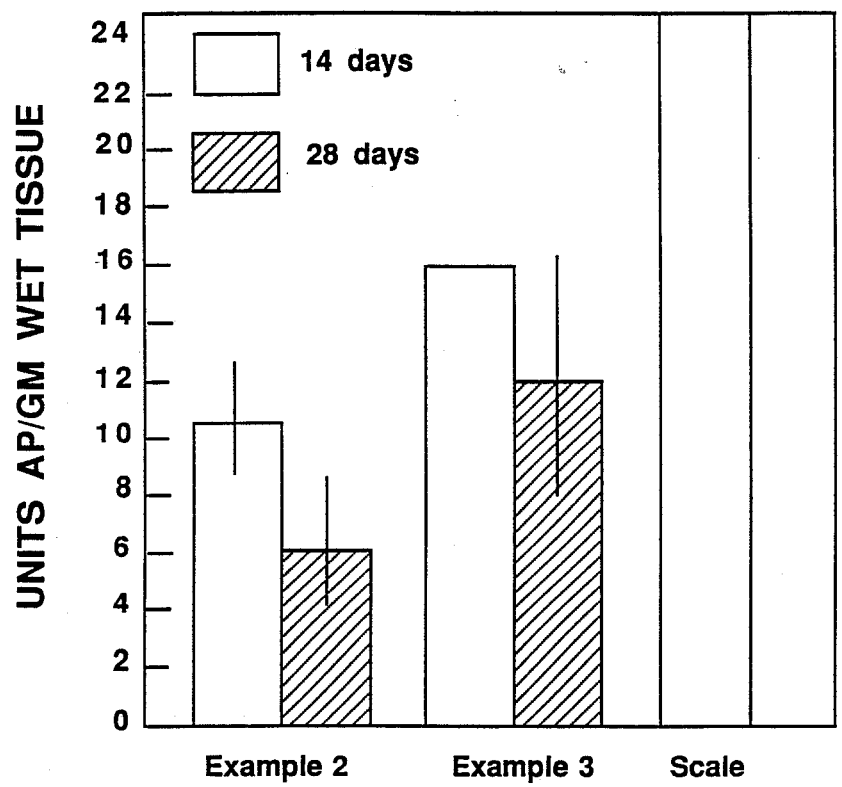
FIG. 2 shows the bone formation activity of the compositions of the invention using alkaline phosphatase as an index.

The levels of alkaline phosphatase (AP) activity are shown in FIG. 2 for 14 and 28 days after implantation. All of the OFE containing compositions gave high levels of AP activity after 14 days. After 28 days, all levels had decreased, as would be expected during the completion of the bone formation process; however, the "Example 3" material shows noticeably higher levels.

Histological Examination

Figure 3A:
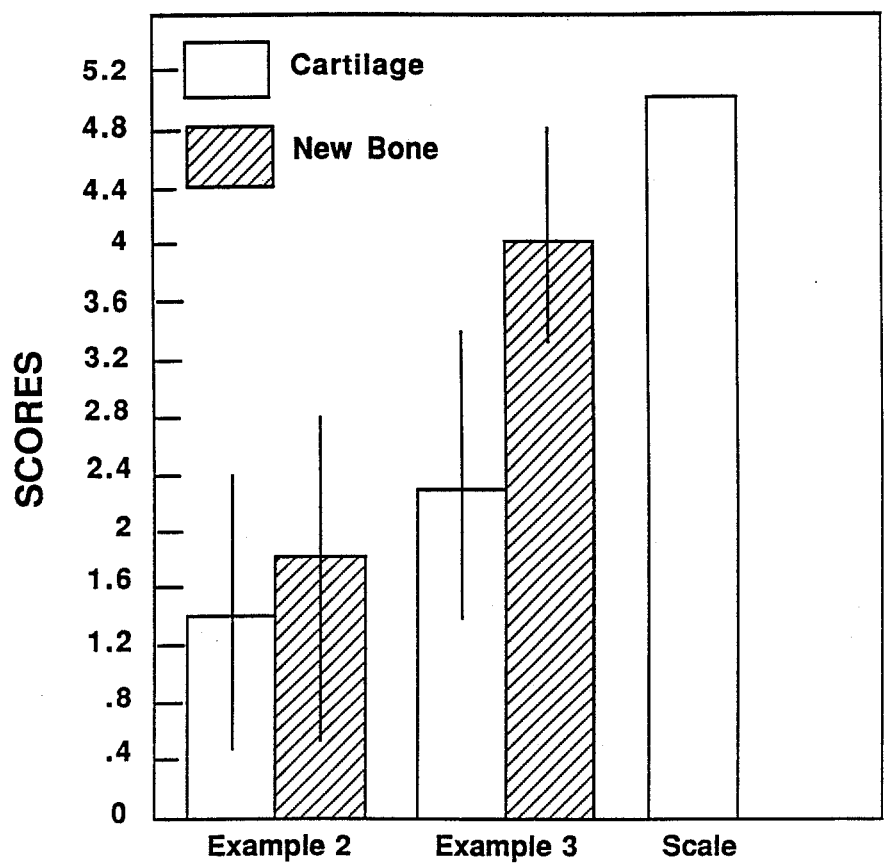
FIGS. 3A and 3B show bone growth results of these compositions using histological evaluation as a criterion.
Figure 3B:
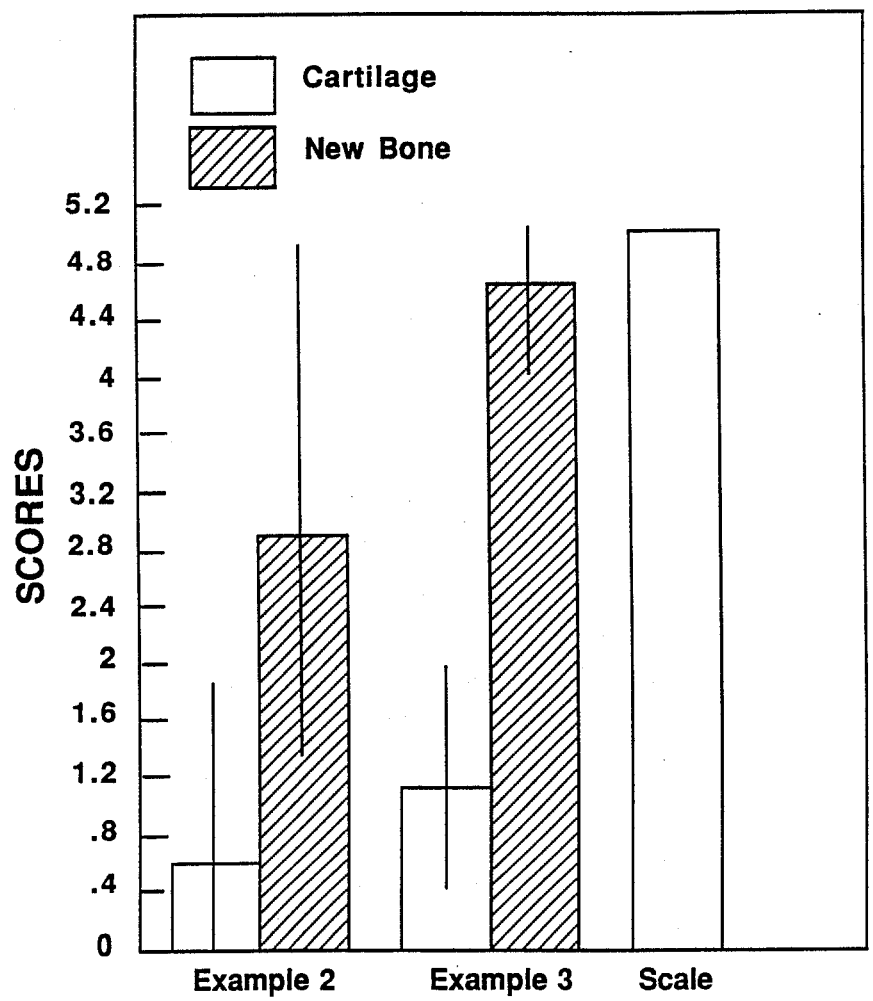

The results of the histological examination of the explants are shown in FIG. 3A (14 days) and 3B (28 days). All samples containing OFE showed moderate to good cartilage and bone formation at 14 days. By 28 days, there was good bone formation and marrow differentiation. At both time points, the composition of the invention made according to Example 3 appeared to encourage bone formation more effectively than the material made without air drying according to Example 2.

What is claimed is:

1. A process for preparing a hypoimmunogenic composition suitable for implantation to effect bone repair in a vertebrate
wherein the composition comprises an osteoinductively effective amount of a protein osteoinductive factor (OF), which OF is sufficiently pure to be hypoimmunogenic in a xenogeneic host, and a carrier having components which consist essentially of mineral constituting 60-98% and collagen constituting 2-40% of the composition,
which process comprises:

(a) preparing a uniform suspension in water of the collagen, mineral, and OF components of the composition so that the concentration of collagen in the suspension is 30-100 mg/ml; and
(b) subjecting the suspension to controlled drying under ambient pressure to obtain a rigid solid.

2. The process of claim 1 wherein the carrier is 75-95% mineral and 5-25% of collagen.

3. The process of claim 1 wherein the drying is conducted in air at a temperature of 1°-40° C.

4. The process of claim 1 wherein the drying is conducted in air at a temperature of 15°-37° C.

5. The process of claim 1 wherein the drying is continued until the solid has a compressive modulus of at least $20N/cm^2$.

6. The process of claim 1, which further includes heat curing of the product of (b).

7. The process of claim 6 wherein the heat curing is conducted until the solid has a compressive modulus of at least $50N/cm^2$.

8. The process of claim 6 wherein the heat curing is conducted at 50°-120° C. for 4-168 hours.

9. The process of claim 1 wherein the suspension of (a) is prepared by mixing a dilute solution of OF with mineral particles, drying the mixture, and mixing the dried mixture with reconstituted atelopeptide fibrillar collagen suspension containing 30-100 mg/ml of collagen.

10. The process of claim 9 wherein the mixture of the solution of OF and mineral particles is dried by air drying.

11. The process of claim 9 wherein the mixture of the solution of OF and mineral particles is dried by lyophilization.

12. The process of claim 1 wherein the suspension of (a) is prepared by adding a solution of OF to collagen in solution, precipitating the collagen and OF, resuspending the precipitate to a collagen concentration of 30-100 mg/ml, and then mixing the resulting suspension with mineral particles.

13. A bone repair composition prepared according to the process of claim 1.

14. A bone repair composition prepared according to the process of claim 2.

15. A bone repair composition prepared according to the process of claim 6.

16. A hypoimmunogenic composition suitable for implantation to effect bone repair in a vertebrate, which consists essentially of 60-98% mineral particles; 2-40% of atelopeptide hypoimmunogenic collagen; and an effective amount of an OF preparation,
wherein the implant is a porous rigid solid of compressive modulus greater than $20N/cm^2$, is homogeneous with respect to its components, and wherein the OF is in a biologically active and available form.

17. The composition of claim 16 having a compressive modulus greater than $50N/cm^2$.

18. The composition of claim 16 wherein the effective amount of OF preparation is 0.5%-4% of partially purified OFE or its equivalent.

19. The composition of claim 18 wherein the effective amount of OF preparation is 0.5%-4% of partially purified OFE.

20. The composition of claim 16 wherein the composition consists essentially of 75-95% mineral particles; 5-25% of atelopeptide hypimmunogenic collagen; and an effective amount of an OF preparation.

* * * * *